(12) United States Patent
Bae et al.

(10) Patent No.: US 9,267,161 B2
(45) Date of Patent: Feb. 23, 2016

(54) *CORYNEBACTERIUM* SP. TRANSFORMED WITH A FRUCTOKINASE GENE DERIVED FROM *ESCHERICHIA* SP. AND PROCESS FOR PREPARING L-AMINO ACID USING THE SAME

(75) Inventors: Hyun Won Bae, Seoul (KR); Hyung Joon Kim, Seoul (KR); Jun Ok Moon, Seoul (KR); Jae Woo Jang, Gyeonggi-do (KR); Jong Chul Kim, Gyeonggi-do (KR); Tae Han Kim, Gyeonggi-do (KR); Jin Suck Sung, Gyeonggi-do (KR); Kyung Han Lee, Seoul (KR); Dae Cheol Kim, Gyeonggi-do (KR); Hyo Jin Kim, Seoul (KR); Hyun Ae Bae, Seoul (KR); Sang Jo Lim, Incheon (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 14/007,941

(22) PCT Filed: Apr. 2, 2012

(86) PCT No.: PCT/KR2012/002474
§ 371 (c)(1),
(2), (4) Date: Sep. 26, 2013

(87) PCT Pub. No.: WO2012/134253
PCT Pub. Date: Oct. 4, 2012

(65) Prior Publication Data
US 2014/0099680 A1    Apr. 10, 2014

(30) Foreign Application Priority Data
Apr. 1, 2011   (KR) .................. 10-2011-0030392

(51) Int. Cl.
*C12P 13/14*   (2006.01)
*C12N 9/12*    (2006.01)
(Continued)

(52) U.S. Cl.
CPC ............... *C12P 13/14* (2013.01); *C12N 9/1205* (2013.01); *C12P 13/04* (2013.01); *C12P 13/08* (2013.01); *C12Y 207/01004* (2013.01)

(58) Field of Classification Search
None
See application file for complete search history.

(56) References Cited

U.S. PATENT DOCUMENTS 7,179,623 B2    2/2007   Livshits et al.
7,736,880 B2 *  6/2010   Park et al. .................. 435/252.1
(Continued)

FOREIGN PATENT DOCUMENTS

EP    2239336    * 10/2010    ............. C12P 13/08
JP    2001-095592 A   4/2001
(Continued)

OTHER PUBLICATIONS

Moon et al., Analyses of enzyme II gene mutants for sugar transport and heterologous expression of fructokinase gene in Corynebacterium glutamicum ATCC 13032., FEMS Microbiol Lett. (2005), vol. 244(2), pp. 259-266.*
(Continued)

*Primary Examiner* — Alexander Kim
(74) *Attorney, Agent, or Firm* — Seed IP Law Group PLLC

(57) ABSTRACT

The present invention relates to *Corynebacterium* sp. that is transformed with an *Escherichia* sp.-derived fructokinase gene to express fructokinase showing a sufficient activity of converting fructose into fructose-6-phosphate, thereby preventing unnecessary energy consumption, and a method for producing L-amino acids using the strain. The transformed *Corynebacterium* sp. of the present invention is able to express fructokinase from the *Escherichia*-derived fructokinase gene to prevent unnecessary energy consumption during fructose metabolism, leading to more cost-effective production of L-amino acids. Therefore, it can be widely used for the effective production of L-amino acids.

11 Claims, 1 Drawing Sheet

(51) Int. Cl.
    *C12P 13/04*    (2006.01)
    *C12P 13/08*    (2006.01)

(56)                References Cited

U.S. PATENT DOCUMENTS 8,323,933   B2*   12/2012   Jang et al.  ............... 435/115
    8,852,903   B2*   10/2014   Eliot et al.  ............... 435/146
    2008/0138859 A1*   6/2008   Park et al.  ............... 435/69.1
    2009/0081740 A1    3/2009   Binder et al.
    2009/0325243 A1   12/2009   Park et al.
    2010/0330624 A1   12/2010   Jang et al.
    2011/0111466 A1    5/2011   Ju et al.
    2012/0208245 A1    8/2012   Rah et al.

FOREIGN PATENT DOCUMENTS

JP      2001-346578 A     12/2001
    JP      2007-151550 A      6/2007
    JP      2009-540860 A     11/2009
    KR       10-0564805 B1     3/2006
    KR      1020080034334 A    4/2008
    WO      2009/125992 A2    10/2009
    WO      2010/093182 A2     8/2010
    WO      2011/004962 A2     1/2011

OTHER PUBLICATIONS

Eggeling et al., Corynebacterium glutamicum (2005), CRC Press, p. 517.*
Olson et al., Production of tyrosine from sucrose or glucose achieved by rapid genetic changes to phenylalaline-producing *Escherichia coli* strains., Appl Micorbiol Biotechnol (2007), vol. 74, pp. 1031-1040.*
Kornberg "If at first you don't succeed . . . fructose utilization by *Escherichia coli*," Advan. Enzyme Regul. 42:349-360 (2002).
Becker et al., "Amplified Expression of Fructose 1,6-Bisphosphatase in *Corynebacterium glutamicum* Increases In Vivo Flux through the Pentose Phosphate Pathway and Lysine Production on Different Carbon Sources," *Applied and Environmental Microbiology*, 71(12):8587-8596 (Dec. 2005).
Lindner et al., "Impact of a new glucose utilization pathway in amino acid-producing *Corynebacterium glutamicum*," *Bioengineered Bugs*, 2(5):291-295 (Sep./Oct. 2011).
Rittmann et al., "Engineering of a Glycerol Utilization Pathway for Amino Acid Production by *Corynebacterium glutamicum*," *Applied and Environmental Microbiology*, 74(20):6216-6222 (Oct. 2008).

* cited by examiner

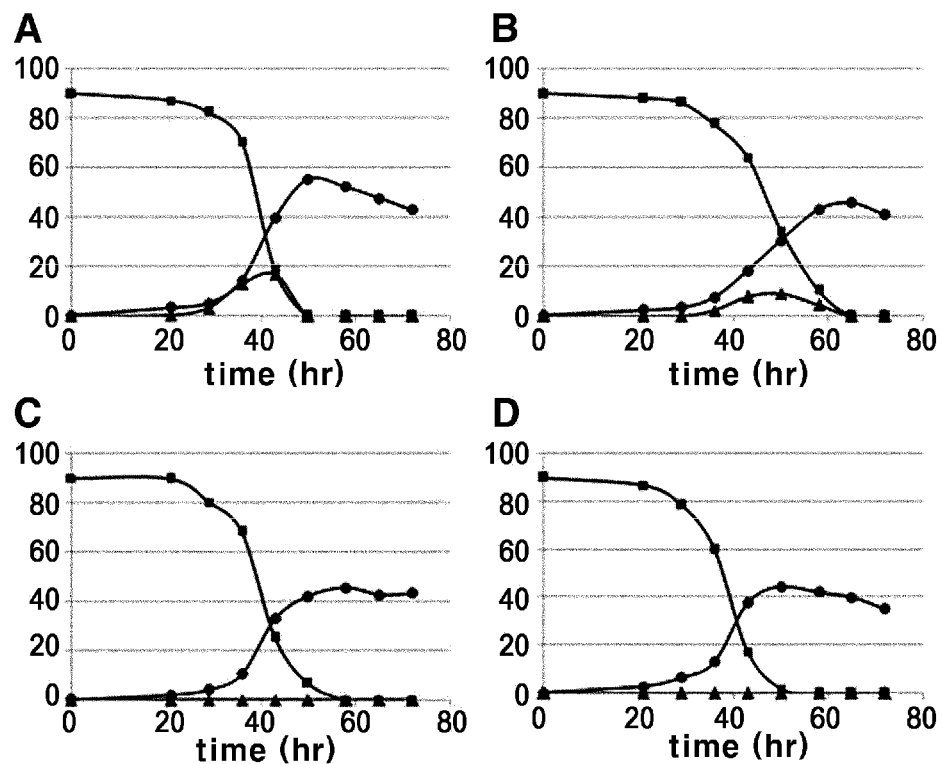

SEQUENCE LISTING

```
<160> NUMBER OF SEQ ID NOS: 21

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
gcgaattcga aaatggggat aga                                            23

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
gcactagtat tacctgcctg tcg                                            23

<210> SEQ ID NO 3
<211> LENGTH: 26
<212> TYPE: DNA
<213> ORGANISM: Artificial Sequence
<220> FEATURE:
<223> OTHER INFORMATION: primer

<400> SEQUENCE: 3
cagaattcac gtgcgttaac gcatcg                                         26
```

```
<210> SEQ ID NO 4
<211> LENGTH: 26
<212> TYPE: DNA
<213> ORGANISM: Artificial Sequence
<220> FEATURE:
<223> OTHER INFORMATION: primer

<400> SEQUENCE: 4
ctactagtca ccttttgtag gcctga                                            26

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
atgccatatg tcagccaaag tatg                                              24

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
atgcactagt attacctgcc tgtcg                                             25

<210> SEQ ID NO 7
<211> LENGTH: 25
<212> TYPE: DNA
<213> ORGANISM: Artificial Sequence
<220> FEATURE:
<223> OTHER INFORMATION: primer

<400> SEQUENCE: 7
atgcactagt atagggagcg ttgac                                             25

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
atgccatatg tgtttccttt cg                                                22

<210> SEQ ID NO 9
<211> LENGTH: 26
<212> TYPE: DNA
<213> ORGANISM: Artificial Sequence
<220> FEATURE:
<223> OTHER INFORMATION: primer

<400> SEQUENCE: 9
ttcatatgtg tgcacctttc gatcta                                            26

<210> SEQ ID NO 10
<211> LENGTH: 28
<212> TYPE: DNA
<213> ORGANISM: Artificial Sequence
<220> FEATURE:
<223> OTHER INFORMATION: primer
```

```
<400> SEQUENCE: 10
ttactagtga ttgttaatgc cgatgcta                                    28

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
ttcctcgagg aggggaactt gatcagagga                                  30

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
ttcctcgagc tacacagctg cccatttgtg                                  30

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
ttcgtcgacg attaaggatt tcaactgcgg                                  30

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
ttcgtcgacg caacgagcaa ttccgagagc                                  30

<210> SEQ ID NO 15
<211> LENGTH: 27
<212> TYPE: DNA
<213> ORGANISM: Artificial Sequence
<220> FEATURE:
<223> OTHER INFORMATION: primer

<400> SEQUENCE: 15
atcggatcca agatctagtc atcaatc                                     27

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
cggcaaggat cctcctgagt g                                           21
```

<210> SEQ ID NO 17
<211> LENGTH: 1285
<212> TYPE: DNA
<213> ORGANISM: Artificial sequence
<220> FEATURE:
<223> OTHER INFORMATION: synthetic gene sequence cscK

<400> SEQUENCE: 17

| | | | | | |
|---|---|---|---|---|---|
| gaaaatgggg | atagaaagtg | ttaccccggt | gctcatgaag | ttttgctagt | gcgttttgcg | 60 |
| ccgcatgcaa | tcgagtttgc | gtcatttttaa | tcatccaggt | taagcaaatt | tggtgaattg | 120 |
| ttaacgttaa | cttttataaa | aataaagtcc | cttactttca | taaatgcgat | gaacatcaca | 180 |
| aatgttaacg | ttaactatga | cgttttgtga | tcgaatatgc | atgttttagt | aaatccatga | 240 |
| cgattttgcg | aaaaagaggt | ttatcactat | gcgtaagtca | gatgaattta | agggaaaaaa | 300 |
| atgtcagcca | agtatgggt | tttaggggat | gcggtcgtag | atctcttgcc | agaatcagac | 360 |
| gggcggctac | tgccttgtcc | tggcggcgcg | ccagctaacg | ttgcggtggg | aatcgccaga | 420 |
| ttaggcggaa | taagtgggtt | tataggtcgg | gtcggtgatg | atccttttgg | ggcgttaatg | 480 |
| caaagaacgc | tgctaactga | gggagtcgat | atcacgtatc | tgaagcaaga | tgaatggcac | 540 |
| cggacatcca | cggtgcttgt | cgatctgaac | gatcaagggg | aacgttcatt | tacgtttatg | 600 |
| gtccgcccca | gtgccgatct | tttttagag | acgacagact | tgccctgctg | gcgacatggc | 660 |
| gaatggttac | atctctgttc | aattgcgttg | tctgccgagc | cttcgcgtac | cagcgcattt | 720 |
| actgcgatga | cggcgatccg | gcatgccgga | ggttttgtca | gcttcgatcc | taatattcgt | 780 |
| gaagatctat | ggcaagacga | gcatttgctc | cgcttgtgtt | tgcggcaggc | gctacaactg | 840 |
| gcggatgtcg | tcaagctctc | ggaagaagaa | tggcgactta | tcagtggaaa | aacacagaac | 900 |
| gatcgggata | tatgcgccct | ggcaaaagag | tatgagatcg | ccatgctgtt | ggtgactaaa | 960 |
| ggtgcagaag | gtgtggtggt | ctgttatcga | ggacaagttc | accattttgc | tggaatgtct | 1020 |
| gtgaattgtg | tcgatagcac | ggggcggga | gatgcgttcg | ttgccgggtt | actcacaggt | 1080 |
| ctgtcctcta | cgggattatc | tacagatgag | agagaaatgc | gacgaattat | cgatctcgct | 1140 |
| caacgttgcg | gagcgcttgc | agtaacggcg | aaaggggcaa | tgacagcgct | gccatgtcga | 1200 |
| caagaactgg | aatagtgaga | agtaaacggc | gaagtcgctc | ttatctctaa | ataggacgtg | 1260 |
| aatttttaa | cgacaggcag | gtaat | | | | 1285 |

<210> SEQ ID NO 18
<211> LENGTH: 1279
<212> TYPE: DNA
<213> ORGANISM: Artificial sequence
<220> FEATURE:
<223> OTHER INFORMATION: synthetic gene sequence mak

<400> SEQUENCE: 18

| | | | | | |
|---|---|---|---|---|---|
| acgtgcgtta | acgcatcgct | gtgcgatccc | atcggaggaa | cccagcccat | cttcgccatg | 60 |
| tcctggctgc | cgcatgggt | aaatgccatc | gaggctagct | gtttttccat | ctcttctgca | 120 |
| cgcagcgaaa | tctcgcggct | aagacggtaa | accattaaat | ttttgaacca | cagcatgata | 180 |
| atttccacgg | ccttgtcgtt | aaatttagcg | ggcatgataa | cgaattgtcg | gcggccttgc | 240 |
| attgccaatc | cggttgtccg | tctctacgct | attgatattg | aaaaaaataa | ggagagtcat | 300 |
| atgcgtatag | gtatcgattt | aggcggcacc | aaaactgaag | tgattgcact | gggcgatgca | 360 |
| ggggagcagt | tgtaccgcca | tcgtctgccc | acgccgcgtg | atgattaccg | gcagactatt | 420 |
| gaaacgatcg | ccacgttggt | tgatatggcg | gagcaggcga | cggggcagcg | cggaacggta | 480 |

| | |
|---|---|
| ggtatgggca ttcctggctc aatttcgcct tacaccggtg tggtgaagaa tgccaattca | 540 |
| acctggctca acggtcagcc attcgataaa gacttaagcg cgaggttgca gcgggaagtg | 600 |
| cggctggcaa atgacgctaa ctgtctggcg gtttcagaag cagtagatgg cgcggcagcg | 660 |
| ggagcgcaga cggtatttgc cgtgattatc ggcacgggat gcggcgcggg cgtggcattc | 720 |
| aatgggcggg cgcatatcgg cggcaatggc acggcaggtg agtggggaca caatccgcta | 780 |
| ccgtggatgg acgaagacga actgcgttat cgcgaggaag tcccttgtta ttgcggtaaa | 840 |
| caaggttgta ttgaaacctt tatttcgggc acggattccg cgatggatta tcgtcgtttg | 900 |
| agcggacatg cgctgaaagg cagtgaaatt atccgcctgg ttgaagaaag cgatccggta | 960 |
| gcggaactgg cattgcgtcg ctacgagctg cggctggcaa atcgctggc acatgtcgtg | 1020 |
| aatattctcg atccggatgt gattgtcctg ggggcggga tgagcaatgt agaccgttta | 1080 |
| tatcaaacgg ttgggcagtt gattaaacaa tttgtcttcg gcggcgaatg tgaaacgccg | 1140 |
| gtgcgtaagg cgaagcacgg tgattccagc ggcgtacgcg cgctgcgtg gttatggcca | 1200 |
| caagagtaaa aaacgtaggc aattggcgca tcatgcctga tgcgacgctt gccgcgtctt | 1260 |
| atcaggccta caaaaggtg | 1279 |

<210> SEQ ID NO 19
<211> LENGTH: 3240
<212> TYPE: DNA
<213> ORGANISM: Artificial sequence
<220> FEATURE:
<223> OTHER INFORMATION: synthetic gene sequence hom-thrB

<400> SEQUENCE: 19

| | |
|---|---|
| gagggggaact tgatcagagg aatacaccat ggagccgatg tcagaggcga ctgcgggcag | 60 |
| atccttttga agctgtttca caatttcttt gcccagttcg cggcggatct ggaaccactt | 120 |
| ttgcatgcga tcgtcgtcag agtggttcat gtgaaaaata cactcaccat ctcaatggtc | 180 |
| atggtgaagg cctgtactgg ctgcgacagc atggaactca gtgcaatggc tgtaaggcct | 240 |
| gcaccaacaa tgattgagcg aagctccaaa atgtcctccc cggggttgata ttagatttca | 300 |
| taaatatact aaaaatcttg agagtttttc cgttgaaaac taaaaagctg ggaaggtgaa | 360 |
| tcgaatttcg gggcttttaaa gcaaaaatga acagcttggt ctatagtggc taggtaccct | 420 |
| tttttgttttg gacacatgta gggtggccga aacaaagtaa taggacaaca acgctcgacc | 480 |
| gcgattattt ttggagaatc atgaccctcag catctgcccc aagctttaac cccggcaagg | 540 |
| gtcccggctc agcagtcgga attgcccttt taggattcgg aacagtcggc actgaggtga | 600 |
| tgcgtctgat gaccgagtac ggtgatgaac ttgcgcaccg cattggtggc ccactggagg | 660 |
| ttcgtggcat tgctgttct gatatctcaa agccacgtga aggcgttgca cctgagctgc | 720 |
| tcactgagga cgcttttgca ctcatcgagc gcgaggatgt tgacatcgtc gttgaggtta | 780 |
| tcggcggcat tgagtaccca cgtgaggtag ttctcgcagc tctgaaggcc ggcaagtctg | 840 |
| ttgttaccgc caataaggct cttgttgcag ctcactctgc tgagcttgct gatgcagcgg | 900 |
| aagccgcaaa cgttgacctg tacttcgagg ctgctgttgc aggcgcaatt ccagtggttg | 960 |
| gcccactgcg tcgctccctg ctggcgatc agatccagtc tgtgatgggc atcgttaacg | 1020 |
| gcaccaccaa cttcatcttg gacgccatgg attccaccgg cgctgactat gcagattctt | 1080 |
| tggctgagc aactcgtttg ggttacgccg aagctgatcc aactgcagac gtcgaaggcc | 1140 |
| atgacgccgc atccaaggct gcaatttggg catccatcgc tttccacacc cgtgttacccg | 1200 |
| cggatgatgt gtactgcgaa ggtatcagca acatcagcgc tgccgacatt gaggcagcac | 1260 |

| | |
|---|---|
| agcaggcagg ccacaccatc aagttgttgg ccatctgtga aagttcacc aacaaggaag | 1320 |
| gaaagtcggc tatttctgct cgcgtgcacc cgactctatt acctgtgtcc cacccactgg | 1380 |
| cgtcggtaaa caagtccttt aatgcaatct tgttgaagc agaagcagct ggtcgcctga | 1440 |
| tgttctacgg aaacggtgca ggtggcgcgc caaccgcgtc tgctgtgctt ggcgacgtcg | 1500 |
| ttggtgccgc acgaaacaag gtgcacggtg ccgtgctcc aggtgagtcc acctacgcta | 1560 |
| acctgccgat cgctgatttc ggtgagacca ccactcgtta ccacctcgac atggatgtgg | 1620 |
| aagatcgcgt gggggttttg gctgaattgg ctagcctgtt ctctgagcaa ggaatctccc | 1680 |
| tgcgtacaat ccgacaggaa gagcgcgatg atgatgcacg tctgatcgtg gtcacccact | 1740 |
| ctgcgctgga atctgatctt tcccgcaccg ttgaactgct gaaggctaag cctgttgtta | 1800 |
| aggcaatcaa cagtgtgatc cgcctcgaaa gggactaatt ttactgacat ggcaattgaa | 1860 |
| ctgaacgtcg gtcgtaaggt taccgtcacg gtacctggat cttctgcaaa cctcggacct | 1920 |
| ggctttgaca ctttaggttt ggcactgtcg gtatacgaca ctgtcgaagt ggaaattatt | 1980 |
| ccatctggct tggaagtgga agttttggc gaaggccaag gcgaagtccc tcttgatggc | 2040 |
| tcccacctgg tggttaaagc tattcgtgct ggcctgaagg cagctgacgc tgaagttcct | 2100 |
| ggattgcgag tggtgtgcca caacaacatt ccgcagtctc gtggtcttgg ctcctctgct | 2160 |
| gcagcggcgg ttgctggtgt tgctgcagct aatggtttgg cggatttccc gctgactcaa | 2220 |
| gagcagattg ttcagttgtc ctctgccttt gaaggccacc cagataatgc tgcggcttct | 2280 |
| gtgctgggtg gagcagtggt gtcgtggaca aatctgtcta tcgacggcaa gagccagcca | 2340 |
| cagtatgctg ctgtaccact tgaggtgcag gacaatattc gtgcgactgc gctggttcct | 2400 |
| aatttccacg catccaccga agctgtgcgc cgagtccttc ccactgaagt cactcacatc | 2460 |
| gatgcgcgat ttaacgtgtc ccgcgttgca gtgatgatcg ttgcgttgca gcagcgtcct | 2520 |
| gatttgctgt gggagggtac tcgtgaccgt ctgcaccagc cttatcgtgc agaagtgttg | 2580 |
| cctattacct ctgagtgggt aaaccgcctg cgcaaccgtg gctacgcggc atacctttcc | 2640 |
| ggtgccggcc caaccgccat ggtgctgtcc actgagccaa ttccagacaa ggttttggaa | 2700 |
| gatgctcgtg agtctggcat taaggtgctt gagcttgagg ttgcgggacc agtcaaggtt | 2760 |
| gaagttaacc aaccttaggc ccaacaagga aggccccctt cgaatcaaga aggggggcctt | 2820 |
| attagtgcag caattattcg ctgaacacgt gaaccttaca ggtgcccggc gcgttgagtg | 2880 |
| gtttgagttc cagctggatg cggttgttttt caccgaggct ttcttggatg aatccggcgt | 2940 |
| ggatggcgca gacgaaggct gatgggcgtt tgtcgttgac cacaaatggg cagctgtgta | 3000 |
| gagcgaggga gtttgcttct tcggtttcgg tggggtcaaa gcccatttcg cggaggcggt | 3060 |
| taatgagcgg ggagagggct tcgtcgagtt cttcggcttc ggcgtggtta atgcccatga | 3120 |
| cgtgtgccca ctgggttccg atggaaagtg ctttggcgcg gaggtcgggg ttgtgcattg | 3180 |
| cgtcatcgtc gacatcgccg agcatgttgg ccatgagttc gatcagggtg atgtattctt | 3240 |

<210> SEQ ID NO 20
<211> LENGTH: 2446
<212> TYPE: DNA
<213> ORGANISM: Artificial sequence
<220> FEATURE:
<223> OTHER INFORMATION: synthetic gene sequence thrC

<400> SEQUENCE: 20

| | |
|---|---|
| gccgttgatc attgttcttc acagaggatc agggtagccc tcttacagga aaatatggga | 60 |
| ctttgattcc caatccatgg ctaagtgtga tcatttagat aattgttcga tcgaccgaat | 120 |

-continued

```
gaaatcaccc gttatggaga cctactggaa ttgagcccag aaaccgtcga tgtgtgcctc    180
aacgtagggg taaagccacg gcccgagcag caccagcccg accgcgagca ccgaacaacc    240
aatgagaaca tacaggttcc acttggacac cggcgctgga ttaaggattt caactgcggt    300
gagattcttc ttgttgttgt cctcgagttt cgagaagctg gggtaatcgg gagctgtcat    360
ctttaaagca catcctaaaa ccgacaattg aaagtgatca gcaacacttt agggtatcgc    420
gtgggcgaag tcacctttt caacatattt gagacggtgt ggggagtat tgtgtcaccc     480 cttgggatag ggttatatcc gtggactaca tttcgacgcg tgatgccagc cgtacccctg    540
cccgcttcag tgatattttg ctgggcggtc tagcaccaga cggcggcctg tacctgcctg    600
caacctaccc tcaactagat gatgcccagc tgagtaaatg gcgtgaggta ttagccaacg    660
aaggatacgc agctttggct gctgaagtta tctccctgtt tgttgatgac atcccagtag    720
aagacatcaa ggcgatcacc gcacgcgcct acacctaccc gaagttcaac agcgaagaca    780
tcgttcctgt caccgaactc gaggacaaca tttacctggg ccaccttcc gaaggcccaa     840 ccgctgcatt caaagacatg gccatgcagc tgctcggcga acttttcgaa tacgagcttc    900
gccgccgcaa cgaaaccatc aacatcctgg gcgctacctc tggcgatacc ggctcctctg    960
cggaatacgc catgcgcggc cgcgagggaa tccgcgtatt catgctgacc ccagctggcc   1020 gcatgaccc attccagcaa gcacagatgt ttggccttga cgatccaaac atcttcaaca   1080
tcgccctcga cggcgttttc gacgattgcc aagacgtagt caaggctgtc tccgccgacg   1140
cagaattcaa aaagacaac cgcatcggtg ccgtgaactc catcaactgg gcacgcctta    1200
tggcacaggt tgtgtactac gtttcctcat ggatccgcac cacaaccagc aatgaccaaa    1260
aggtcagctt ctccgtacca accggcaact tcggtgacat ttgcgcaggc cacatcgccc    1320
gccaaatggg acttcccatc gatcgcctca tcgtggccac caacgaaaac gatgtgctcg    1380
acgagttctt ccgtaccggc gactaccgag tccgcagctc cgcagacacc cacgagacct    1440
cctcaccttc gatggatatc tcccgcgcct ccaacttcga gcgtttcatc ttcgacctgc    1500
tcggccgcga cgccacccgc gtcaacgatc tatttggtac ccaggttcgc caaggcggat    1560
tctcactggc tgatgacgcc aactttgaga aggctgcagc agaatacggt ttcgcctccg    1620
gacgatccac ccatgctgac cgtgtggcaa ccatcgctga cgtgcattcc cgcctcgacg    1680
tactaatcga tccccacacc gccgacgcg ttcacgtggc acgccagtgg agggacgagg     1740
tcaacacccc aatcatcgtc ctagaaactg cactcccagt gaaatttgcc gacaccatcg    1800
tcgaagcaat tggtgaagca cctcaaactc cagagcgttt cgccgcgatc atggatgctc    1860
cattcaaggt ttccgaccta ccaaacgaca ccgatgcagt taagcagtac atagtcgatg    1920
cgattgcaaa cacttccgtg aagtaacttg ctttacgcca aggcctgatt cctctcttta    1980
tgggatggaa ccaggccttt cgcattgagt ggcgttttaa ggcctccaat tcttagaacg    2040
ggtgtttgac atggaggggt cacagtcaag ccgttagaag cgattctggg agggcaagtt    2100
tttcggagtt ggaggtcgaa tttccgctga actgatggga accagacagg cgtgacaaga    2160
ttggctaaaa acctgaagtt ttgtcacgcc tgtctggttt ccctcttgtc ggtgcgagcg    2220
agtcccttga acgacacaga tcgcgccaaa tggaagtgtc tgcgaccca gaatatttga     2280 ttccccggtc cgagtcgtgc gaaaaatgct ctggttagtc ctcgatcatc gcaatcgcat    2340
caatttccac agttgcacca taaggaagcg atgatgcacc cacgaaagag cgtgccgggc    2400
ggccttcgag gaaatgctct cggaattgct cgttgcattc ttcgcg                   2446
```

<210> SEQ ID NO 21
<211> LENGTH: 2470
<212> TYPE: DNA
<213> ORGANISM: Artificial sequence
<220> FEATURE:
<223> OTHER INFORMATION: synthetic gene sequence thrE

<400> SEQUENCE: 21

| | | | | | |
|---|---|---|---|---|---|
| cagcaagatc | tagtcatcaa | tctggtcaac | gaatttaagg | agcttaattt gaacacgcca | 60 |
| tatgaaaagt | gactaatttc | aacccaaacg | ggagcctaag | tgaaatgaaa taatcccctc | 120 |
| accaactggc | gacattcaaa | caccgtttca | tttccaaaca | tcgagccaag ggaaaagaaa | 180 |
| gcccctaagc | cccgtgttat | taaatggaga | cttttggag | acctcaagcc aaaaagggc | 240 |
| attttcatta | agaaaatacc | cctttgacct | ggtgttattg | agctggagaa gagacttgaa | 300 |
| ctctcaacct | acgcattaca | agtgcgttgc | gctgccaatt | cgccactcc agcaccgcag | 360 |
| atgctgatga | tcaacaacta | cgaatacgta | tcttagcgta | tgtgtacatc acaatggaat | 420 |
| tcggggctag | agtatctggt | gaaccgtgca | taaacgacct | gtgattggac tcttttcct | 480 |
| tgcaaaatgt | tttccagcgg | atgttgagtt | ttgcgaccct | tcgtggccgc atttcaacag | 540 |
| ttgacgctgc | aaaagccgca | cctccgccat | cgccactagc | cccgattgat ctcactgacc | 600 |
| atagtcaagt | ggccggtgtg | atgaatttgg | ctgcgagaat | tggcgatatt ttgctttctt | 660 |
| caggtacgtc | aaatagtgac | accaaggtac | aagttcgagc | agtgacctct gcgtacggtt | 720 |
| tgtactacac | gcacgtggat | atcacgttga | atacgatcac | catcttcacc aacatcggtg | 780 |
| tggagaggaa | gatgccggtc | aacgtgtttc | atgttgtagg | caagttggac accaacttct | 840 |
| ccaaactgtc | tgaggttgac | cgtttgatcc | gttccattca | ggctggtgcg accccgcctg | 900 |
| aggttgccga | gaaaatcctg | gacgagttgg | agcaatcccc | tgcgtcttat ggtttccctg | 960 |
| ttgcgttgct | tggctgggca | atgatgggtg | gtgctgttgc | tgtgctgttg ggtggtggat | 1020 |
| ggcaggtttc | cctaattgct | tttattaccg | cgttcacgat | cattgccacg acgtcatttt | 1080 |
| tgggaaagaa | gggtttgcct | acttcttcc | aaaatgttgt | tggtggtttt attgccacgc | 1140 |
| tgcctgcatc | gattgcttat | tctttggcgt | tgcaatttgg | tcttgagatc aaaccgagcc | 1200 |
| agatcatcgc | atctggaatt | gttgtgctgt | tggcaggttt | gacactcgtg caatctctgc | 1260 |
| aggacggcat | cacgggcgct | ccggtgacag | caagtgcacg | atttttcgaa acactcctgt | 1320 |
| ttaccggcgg | cattgttgct | ggcgtgggtt | tgggcattca | gctttctgaa atcttgcatg | 1380 |
| tcatgttgcc | tgccatggag | tccgctgcag | cacctaatta | ttcgtctaca ttcgcccgca | 1440 |
| ttatcgctgg | tggcgtcacc | gcagcggcct | tcgcagtggg | ttgttacgcg gagtggtcct | 1500 |
| cggtgattat | tgcggggctt | actgcgctga | tgggttctgc | gttttattac ctcttcgttg | 1560 |
| tttatttagg | ccccgtctct | gccgctgcga | ttgctgcaac | agcagttggt ttcactggtg | 1620 |
| gtttgcttgc | ccgtcgattc | ttgattccac | cgttgattgt | ggcgattgcc ggcatcacac | 1680 |
| caatgcttcc | aggtctagca | atttaccgcg | gaatgtacgc | caccctgaat gatcaaacac | 1740 |
| tcatggggttt | caccaacatt | gcggttgctt | tagccactgc | ttcatcactt gccgctggcg | 1800 |
| tggtttggg | tgagtggatt | gcccgcaggc | tacgtcgtcc | accacgcttc aacccatacc | 1860 |
| gtgcatttac | caaggcgaat | gagttctcct | tccaggagga | agctgagcag atcagcgcc | 1920 |
| ggcagagaaa | acgtccaaag | actaatcaga | gattcggtaa | taaaaggtaa aaatcaacct | 1980 |
| gcttaggcgt | ctttcgctta | aatagcgtag | aatatcgggt | cgatcgcttt taaacactca | 2040 |
| ggaggatcct | tgccggccaa | aatcacggac | actcgtccca | ccccagaatc ccttcacgct | 2100 |

```
gttgaagagg aaaccgcagc cggtgcccgc aggattgttg ccacctattc taaggacttc    2160
ttcgacggcg tcactttgat gtgcatgctc ggcgttgaac ctcagggcct gcgttacacc    2220
aaggtcgctt ctgaacacga ggaagctcag ccaaagaagg ctacaaagcg gactcgtaag    2280
gcaccagcta agaaggctgc tgctaagaaa acgaccaaga agaccactaa gaaaactact    2340
aaaaagacca ccgcaaagaa gaccacaaag aagtcttaag ccggatctta tatggatgat    2400
tccaatagct ttgtagttgt tgctaaccgt ctgccagtgg atatgactgt ccacccagat    2460
ggtagctata                                                          2470
```

CORYNEBACTERIUM SP. TRANSFORMED WITH A FRUCTOKINASE GENE DERIVED FROM ESCHERICHIA SP. AND PROCESS FOR PREPARING L-AMINO ACID USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_416USPC_SEQUENCE_LISTING.txt. The text file is 17.6 KB, was created on Dec. 11, 2013, and is being submitted electronically via EFS-Web.

TECHNICAL FIELD

The present invention relates to *Corynebacterium* sp. transformed with an *Escherichia* sp.-derived gene and a method for producing L-amino acids using the strain.

BACKGROUND ART

*Corynebacterium* sp., in particular, *Corynebacterium glutamicum*, is a Gram-positive microorganism used for the production of L-amino acids. L-amino acids such as L-lysine have been widely used for the production of animal feeds, medicines for humans, pharmaceutical industry, etc, and are mass-produced by a genetic engineering method using a *Corynebacterium* strain. Increasing demand for L-amino acids due to industrial development has led to the development of improved *Corynebacterium* strains for more effective and economical production of L-amino acids.

In general, the L-amino acid production of *Corynebacterium* has been enhanced by introduction of particular DNA, such as L-amino acid biosynthesis-related genes, into a *Corynebacterium* strain or by improvement of its activity. For example, Korean Patent Publication Nos. 2001-51915 and 2001-62279 disclose methods for enhancing the productivity of L-amino acid from *Corynebacterium* by the under-expression of sucC and sucD gene and zwa2 gene derived from *Corynebacterium glutamicum*. Korean Patent Publication No. 2001-62272 discloses a method for enhancing the productivity of L-amino acid from *Corynebacterium* by the over-expression of zwa1 gene derived from *Corynebacterium glutamicum*. Japanese Patent No. 1995-121228 discloses a method for introducing a gene encoding citric acid synthase derived from *Escherichia coli*.

Meanwhile, *Corynebacterium* sp. is able to utilize sucrose, glucose, and fructose as carbon sources. Among them, sucrose is phosphorylated by a phosphotransferase system (PTS) and transported into the cell. Subsequently, phosphorylated sucrose is hydrolyzed by invertase to glucose-6-phosphate and fructose. The produced glucose-6-phosphate enters glycolysis, but unphosphorylated fructose is exported from the cell. It is phosphorylated by a PTS, and then transported into the cell, and utilized in glycolysis. Utilization of fructose as a carbon source requires a relatively complex metabolic pathway, because *Corynebacterium* sp. has no fructokinase activity (Appl Environ Microbiol. (1996) 62:3878-3880). On the other hand, in fructokinase-expressing bacteria, sucrose is hydrolyzed by invertase to glucose-6-phosphate and fructose, and fructose is phosphorylated by fructokinase. Subsequently, glucose-6-phosphate and phosphorylated fructose can enter the glycolytic pathway.

The use of fructose as a carbon source for the cultivation of *Corynebacterium* sp. has a problem in that it requires unnecessary energy consumption due to the complex metabolic pathway, and thus many studies have been conducted to solve this problem. For example, the present inventors developed a method of producing L-lysine using a transformed strain that is prepared by introduction of a fructokinase gene derived from *Clostridium acetobutylicum* or *Bacillus subtilis* into *Corynebacterium* sp. (Korean Patent No. 564805). However, subsequent studies showed that *Corynebacterium* sp. transformed with the fructokinase gene has very low fructokinase activity, and upon the use of sucrose as a carbon source for the cultivation of *Corynebacterium* sp., a portion of the fructose derived from sucrose is converted into fructose-6-phosphate, and the rest is phosphorylated by a PTS outside the cell and subsequently transported into the cell, like in the wild-type, and thus the introduction of the fructokinase gene does not provide a sufficient outcome. Therefore, there is a need to explore other fructokinase genes that show sufficient activity of converting fructose into fructose-6-phosphate in *Corynebacterium* sp.

The desired fructokinase genes were identified, resulting from the studies on genes mediating sucrose uptake and hydrolysis to impart a sucrose-assimilating ability, and are exemplified by scr regulon found in *Salmonella*, Klebsiella pneumonia, and *Erwinia amylovora* (J. Bacteriol., 151:68-76, 1982; Mol. Microbiol., 2:1-8, 1988; J. Bacteriol., 173: 7464-7470, 1991; J. Gen. Microbiol., 134:1635-1644, 1988; J. Bacteriol., 182:5351-5358, 2000; U.S. Pat. No. 7,179,623), cscregulon derived from *Escherichia* sp. (Appl. Environ. Microbiol., 58:2081-2088, 1992; U.S. Pat. No. 6,960,455), and scr regulon and sac operon derived from Gram-positive microorganism, *Streptococcus mutans* (J. Bacteriol., 171:263-271, 1989). Among them, two fructokinase genes (cscK and mak) were found in *Escherichia* sp. cscK is a fructokinase gene belonging to csc regulon, and is known to be involved in sucrose metabolism, together with cscB (proton symport-type sucrose permease) and cscA (sucrose hydolase) (J. Bacteriol., 184: 5307-5316, 2002). mak is a gene encoding mannokinase, and the mannokinase is known to have an activity of converting hexose such as mannose, fructose, and glucose into a 6-phospho-ester form (Mol. Microbiol., 5:2913-2922, 1991).

DISCLOSURE

Technical Problem

Accordingly, the present inventors isolated fructokinase genes (cscK and mak) of *Escherichia*, and transformed a *Corynebacterium* strain with the genes to provide a strain having improved amino acid productivity, thereby completing the present invention.

Technical Solution

An object of the present invention is to provide *Corynebacterium* sp. that is transformed with an *Escherichia* sp.-derived fructokinase gene to express fructokinase showing a sufficient activity of converting fructose into fructose-6-phosphate in the cell without re-entry after export of intracellular fructose produced by hydrolysis of phosphorylated sucrose, thereby preventing unnecessary energy consumption.

Another object of the present invention is to provide a method for producing an L-amino acid, comprising the steps of culturing the transformed *Corynebacterium* sp., and collecting the L-amino acid therefrom.

Still another object of the present invention is to provide a method for producing an L-amino acid, comprising the steps of culturing the transformed *Corynebacterium* sp. in a medium containing sucrose as a carbon source, and collecting the L-amino acid therefrom.

Advantageous Effects

The transformed *Corynebacterium* sp. of the present invention is able to express the *Escherichia*-derived fructokinase to prevent unnecessary energy consumption during fructose metabolism, leading to more cost-effective production of L-amino acid. Therefore, it can be widely used for the effective production of L-amino acid.

DESCRIPTION OF DRAWINGS

FIG. 1 is a graph showing the quantification results of sucrose and fructose present in media, after cultivation of *Corynebacterium glutamicum* transformed with fructokinase gene.

BEST MODE

In one aspect, to achieve the above objects, the present invention provides *Corynebacterium* sp. for producing L-amino acids, comprising an *Escherichia* sp.-derived fructokinase gene operably linked to a gene expression unit. In this regard, the fructokinase gene is not particularly limited, and is preferably cscK or mak, and is most preferably cscK. According to one Example of the present invention, the cscK has a nucleotide sequence of SEQ ID NO. 17, and the mak has a nucleotide sequence of SEQ ID NO. 18.

In addition, the gene expression unit is operably linked to a vector, and preferably inserted in *Corynebacterium* microorganism by transformation or incorporated by insertion into the chromosome of *Corynebacterium* microorganism. The gene is preferably overexpressed by modification of gene expression regulatory region.

For example, instead of the intrinsic promoter upstream of the gene, other heterogeneous promoters may be linked, and examples thereof may include a pcj7 promoter, a lysCP1 promoter, an EF-Tu promoter, a groEL promoter, an aceA promoter, and an aceB promoter. A *Corynebacterium*-derived promoter, pcj7 promoter or lysCP1 promoter is preferably used, and pcj7 promoter is most preferably used.

As used herein, the term "expression unit" means a fragment comprising promoter operably linked to a polynucleotide encoding the protein and the polynucleotide, and may further include 3'-UTL, 5'-UTL, poly A tail or the like. As used herein, the term "expression unit" can be interchangeable with "expression cassette".

As used herein, the term "pcj7 promoter" means a promoter that can be expressed to show excellent promoter activity in *Corynebacterium ammoniagenes* and *Escherichia*, and also show excellent promoter activity in *Corynebacterium glutamicum* (Korean Patent No. 0620092).

As used herein, the term "lysCP1 promoter" means a promoter improved by nucleotide substitution of a promoter region of the gene encoding aspartate kinase and aspartate semialdehyde dehydrogenase, and a strong promoter that increases the expression level of aspartate kinase gene to improve the enzymatic activity by approximately 5 times more than the wild-type (WO 2009/096689).

In the present invention, the *Corynebacterium* sp., into which the fructokinase gene can be introduced, may include all strains that belong to *Corynebacterium* sp. and have an ability of producing L-amino acids. Examples thereof may preferably include, but are not limited to, *Corynebacterium glutamicum* (ATCC 13032), *Corynebacterium thermoaminogenes* (FERM BP-1539), *Brevibacterium flavum* (ATCC 14067), *Brevibacterium fermentum* (ATCC 13869), and more preferably *Corynebacterium glutamicum* KFCC10881 (Korean Patent No. 0159812), KFCC-11074, and KFCC110011.

As used herein, the term "transformation" means an overall action of introducing the fructokinase gene into a host cell, *Corynebacterium* sp. for its expression in the host cell. In this regard, the fructokinase gene is a polynucleotide capable of encoding the fructokinase, including DNA and RNA. As long as the gene can be introduced in the host cell and expressed therein, the gene can be introduced in any type. For example, the gene can be introduced into the host cell in an expression cassette which is a polynucleotide expressome including by itself whole elements for expressing the gene. The expression cassette includes a promoter which is operably linked to the gene, a transcription termination signal, a ribosome binding site, and a translation termination signal. The expression cassette may be an expression vector capable of self-replicating. The gene also may be introduced into the host cell by itself or in a polynucleotide expressome to be operably linked to the sequence necessary for expression in the host cell.

Meanwhile, in another aspect, the present invention relates to a method for producing an L-amino acid, comprising the steps of culturing the *Corynebacterium* sp. transformed with the *Escherichia* sp.-derived fructokinase gene; and collecting the L-amino acid from the culture.

In this regard, the L-amino acid may be all types of L-amino acids, and is preferably L-lysine, L-threonine or L-glutamate.

The cultivation of *Corynebacterium* sp. may be performed in a proper medium by various cultivation methods known in the art (Chmiel, Bipprozesstechnik 1. Einfuhrung in die Bioverfahrenstechnik, Gustav Fischer Verlag, Stuttgart, 1991; Storhas, Bioreaktorenundperiphere Einrichtungen, Vieweg Verlag, Braunschweig/Wiesbaden, 1994). Examples of the cultivation method may include batch cultivation, continuous cultivation, and fed-batch cultivation. The fed-batch cultivation includes a fed batch process and a repeated fed batch process, but is not limited thereto.

Moreover, the medium used for the culture herein may be suitably selected by those skilled in the art, depending on cultivation mode and strain ("Manual of Methods for General Bacteriology" by the American Society for Bacteriology, Washington D.C., USA, 1981). The medium used in the present invention includes various carbon sources, nitrogen sources and trace elements. The medium for cultivation of *Corynebacterium* microorganism may include all of sucrose, glucose, fructose, lipid, fatty acid, alcohol, organic acid, etc. In particular, the *Corynebacterium* microorganism of the present invention has a fructokinase activity so as to immediately phosphorylate fructose by fructokinase in the cell without re-entry after export of intracellular fructose produced by hydrolysis of phosphorylated sucrose, and consequently utilizes phosphorylated fructose in glycolysis. Therefore, the *Corynebacterium* microorganism of the present invention has more improved sucrose-assimilating ability than the known *Corynebacterium* microorganisms. Specific examples of the useful carbon sources include carbohydrates such as sucrose-containing molasses, glucose, lactose, fructose, maltose, starch, and cellulose; oil such as soybean oil, sunflower oil, castor oil and coconut oil; fatty acid such as palmitic acid, stearic acid, and linoleic acid; alcohol such as glycerol and ethanol; and organic acids such as acetic acid. A proper amount of carbon source can be used in various ways.

The nitrogen sources include organic nitrogen sources such as peptone, yeast extract, broth, malt extract, corn steep liquor, and soybean meal, and inorganic nitrogen sources such as urea, ammonium sulfate, ammonium chloride, ammonium phosphate, ammonium carbonate and ammonium nitrate. These nitrogen sources may be used singly or in combination. Examples of phosphorus sources useful in the culture media may include dipotassium hydrogen phosphate, potassium dihydrogen phosphate and corresponding sodium salts. Also, culture media may include metal salts such as magnesium sulfate or ferrous sulfate. In addition, amino acids, vitamins, and proper precursors may be included. The medium or the precursor may be added to the culture by batch-type or continuously.

pH of the culture can be adjusted during the cultivation by adding a compound such as ammonium hydroxide, potassium hydroxide, ammonia, phosphoric acid and sulfuric acid by a proper method. The generation of air bubbles can be inhibited during the cultivation by using an antifoaming agent such as fatty acid polyglycol ester. To maintain an aerobic condition in the culture, oxygen or oxygen-containing gas (e.g., air) can be injected into the culture. The temperature of the culture is 20 to 45° C., and preferably 25 to 40° C. The cultivation can be continued until the production of L-amino acid reaches a desired level, and preferably for 10 to 160 hours.

L-amino acid can be isolated from culture media using a typical method known in the art. Examples of the isolation method may include centrifugation, filtration, ion exchange chromatography, crystallization, etc. For example, a biomass can be removed from the culture by low speed centrifugation, and the resulting supernatant can be purified by ion exchange chromatography.

In still another aspect, the present invention relates to a method for producing an L-amino acid, comprising the steps of culturing the above described *Corynebacterium* sp. in a medium containing sucrose, and isolating the L-amino acid from the culture. In this regard, L-amino acid produced by *Corynebacterium* sp. for producing L-amino acids may be, but is not particularly limited to, L-lysine, L-threonine or L-glutamate.

In one embodiment of the present invention, the method for producing L-lysine includes the steps of culturing the above described *Corynebacterium* sp. in a medium containing sucrose, and collecting L-amino acid from the culture.

In another embodiment of the present invention, the method for producing L-threonine includes the steps of introducing an expression vector including a cscK promoter-linked fructokinase gene cscK and a plasmid vector including threonine biosynthesis- and export-related genes into *Corynebacterium glutamicum* KFCC10881, to obtain a transformed strain and then culturing the strain and collecting L-threonine from the culture. In this regard, the expression vector including a cscK promoter-linked fructokinase gene cscK is preferably pDZTn-pcj7_cscK or pDZTn-lysCP1_cscK, but is not particularly limited thereto. The plasmid vector including threonine biosynthesis- and export-related genes is preferably pECCG117-homthrBCE, but is not particularly limited thereto.

In still another embodiment of the present invention, the method for producing L-glutamate includes the steps of introducing an expression vector including a cscK promoter-linked fructokinase gene cscK into a glutamate-producing strain, *Corynebacterium glutamicum* KTCC10774 to obtain a transformed strain and then culturing the strain and collecting L-glutamate from the culture. In this regard, the expression vector including a cscK promoter-linked fructokinase gene cscK is preferably pDZTn-pcj7_cscK or pDZTn-lysCP1_cscK, but is not particularly limited thereto.

According to one Example of the present invention, the introduction of the *Escherichia*-derived fructokinase gene cscK or mak greatly increased L-lysine productivity in comparison to the introduction of the known *Clostridium acetobutyricum*-derived fructokinase gene, CFK (Korean Patent No. 0564805). In particular, when the fructokinase gene cscK linked to the heterogeneous promoter pcj7, or lysCP1 instead of its intrinsic promoter is introduced, the effect was more improved (Table 1). In addition, when the strain transformed by introduction of the fructokinase gene cscK linked to the pcj7 promoter is cultured in a medium containing sucrose as a carbon source, fructose produced by sucrose hydrolysis is not secreted into the medium, and thus fructose produced by intracellular hydrolysis of sucrose present in the medium is completely phosphorylated, and utilized in glycolysis (FIG. 1). Moreover, when the fructokinase gene is introduced, fructokinase activity was increased by 1.95 to 4.24 times, compared to the case of no introduction of the fructokinase gene. When cscK among the fructokinase genes is introduced, fructokinase activity was increased by 1.80 to 2.16 times, compared to the case of the introduction of known fructokinase genes (Table 3).

The strain transformed by the introduction of the *Escherichia*-derived fructokinase gene improves not only L-lysine productivity but also productivity of other L-amino acids, L-threonine (Table 4) and L-glutamate (Table 5). Therefore, the strain transformed by introduction of the *Escherichia*-derived fructokinase gene of the present invention can be used for the production of all L-amino acids.

Accordingly, the present inventors designated a transformant (KFCC-10881-Pcj7_cscK) transformed with pDZTn-pcj7_cscK showing the most excellent effect as *Corynebacterium glutamicum* CA01-2012, and deposited it at the Korean Culture Center of Microorganisms (hereinbelow, abbreviated to "KCCM") on Mar. 28, 2011 under the Accession number KCCM11183P.

MODE FOR INVENTION

Hereinafter, the present invention will be described in more detail with reference to Examples. However, these Examples are for illustrative purposes only, and the invention is not intended to be limited thereby.

EXAMPLE 1

Acquisition of *E. coli*-Derived Fructokinase Gene and Construction of Vector

The base sequence of *E. coli*-derived fructokinase gene was clearly revealed and published. The sequence information of cscK gene (SEQ ID NO. 17) derived from *Escherichia coli* EC3231 (Accession No. X81461) and mak gene (SEQ ID NO. 18) derived from W3110 (Accession No. AC000091) were obtained from the NIH GenBank.

Based on the reported base sequences, primers having a 5'-terminal EcoRI restriction site and a 3'-terminal SpeI restriction site were synthesized, and the chromosome of *E. coli* W strain (ATCC9637) purchased from American Type Culture Collection was used as a template to amplify the cscK gene of approximately 1200 bp containing a promoter region (using the below primers of SEQ ID NOs. 1 and 2) and the mak gene (using the below primers of SEQ ID NOs. 3 and 4) by PCR. At this time, PCR was performed under the conditions including denaturation at 94° C. for 5 min, 30 cycles of denaturation at 94° C. for 30 seconds, annealing at 56° C. for 30 seconds, and polymerization at 72° C. for 1 minute, and then polymerization at 72° C. for 7 minutes.

```
SEQ ID NO. 1:
5'-gcgaattcgaaaatggggataga-3'

SEQ ID NO. 2:
5'-gcactagtattacctgcctgtcg-3'

SEQ ID NO. 3:
5'-cagaattcacgtgcgttaacgcatcg-3'

SEQ ID NO. 4:
5'-ctactagtcacctttttgtaggcctga-3'
```

The two amplified polynucleotides of fructokinase genes were treated with EcoRI and SpeI restriction enzymes. Each DNA fragment was obtained, and then ligated into EcoRI and SpeI sites of pECCG117, which is a shuttle vector of *E. coli* and *Corynebacterium* sp. microorganism. Thereafter, *E. coli* DH5α was transformed with the vector, and spread on an LB solid media containing kanamycin. Colonies transformed with the vector harboring the genes by PCR were selected, and then plasmids were obtained by the known plasmid extraction method, are designated as "pECCG117-cscK" and "pECCG117-mak", respectively.

EXAMPLE 2

Introduction of Fructokinase Gene into Lysine-Producing Strain and Comparison of Lysine Productivity An L-lysine-producing strain, *Corynebacterium glutamicum* KFCC10881 was transformed with the pECCG117-cscK or the pECCG117-mak vector using an electric pulse method, and kanamycin resistant colonies were selected.

The strains transformed with two fructokinase genes derived from *E. coli* and the strain transformed with the above described *Clostridium acetobutyricum*-derived fructokinase CFK (Korean Patent No. 0564805) were cultured, and their lysine productivities were compared.

To 250 ml of a corner-baffle flask containing 25 ml of seed medium (25 μl/ml of kanamycin added), each strain was seeded and cultured by shaking at 200 rpm and 30° C. for 20 hours. At this time, the seed medium (pH 7.0) had the following composition: sucrose 20 g, peptone 10 g, yeast extract 10 g, urea 5 g, $KH_2PO_4$ 4 g, $K_2HPO_4$ 8 g, $MgSO_4$ $7H_2O$ 0.5 g, biotin 100 ug, thiamine HCl 1000 ug (based on 1 L of processing water).

Next, to 250 ml of a corner-baffle flask containing 24 ml of production medium (25 μl/ml of kanamycin added), 1 ml of seed culture liquid was seeded and cultured by shaking at 200 rpm and 30° C. for 72 hours. At this time, the production medium (pH 7.0) had the following composition: sucrose 80 g, molasses or pre-treated molasses (as reducing sugar) 20 g, corn steep liquor 5 g, $(NH_4)_2SO_4$ 40 g, urea 4 g, $KH_2PO_4$ 1 g, NaCl 2.5 g, $MgSO_4$ $7H_2O$ 1 g, $FeSO_4$ $7H_2O$ 10 mg, $MnSO_4$ $5H_2O$ 10 mg, biotin 100 ug, thiamine HCl 200 ug, $CaCO_3$ 40 g, L-leucine 0.4 g if necessary, L-threonine 0.1 g if necessary, L-methionine 0.1 g if necessary (based on 1 L of processing water).

Finally, the cultivation was terminated, and the average concentration of L-lysine was determined by HPLC (see Table 1).

TABLE 1

Comparison of L-lysine concentration according to the introduction of fructokinase gene (unit: g/L)

| Experimental group | Strain | Average concentration of L-lysine |
|---|---|---|
| 1 | KFCC10881/pECCG117 | 32.9 |
| 2 | KFCC10881/pECCG117-cscK | 40.5 |
| 3 | KFCC10881/pECCG117-mak | 35.4 |
| 4 | KFCC10881/pECCG-CFK | 34.1 |

As shown in Table 1, the strains transformed with the fructokinase genes (Experimental groups 2-4) showed higher average concentration of L-lysine than the strain transformed without fructokinase gene (Experimental group 1). Among the strains transformed with the fructokinase genes, the strain transformed with cscK or mak (Experimental groups 2 and 3) showed higher average concentration of L-lysine than the strain transformed with the known fructokinase gene (Experimental group 4).

Therefore, in order to more efficiently produce L-lysine, the use of fructokinase gene derived from *E. coli* is more preferable than the known fructokinase gene.

EXAMPLE 3

Construction of Recombinant Vector for Replacement of cscK Gene Promoter and Chromosomal Introduction In order to introduce the *E. coli*-derived fructokinase gene into the chromosome of *Corynebacterium*, the vector pDZTn (Korean Patent Publication No. 2009-0107665) introduced with the transposon gene of *Corynebacterium* sp. was used as a basic vector. The cscK gene was selected from the two *E. coli*-derived fructokinase genes, because it showed much higher lysine productivity. A strong promoter derived from *Corynebacterium* was linked upstream of the initiation codon of the cscK gene to increase its expression level.

Based on SEQ ID NO. 17, the ORF region was only amplified, and primers (below SEQ ID NOs. 5 and 6) having a 5'-terminal NdeI restriction site and a 3'-terminal SpeI restriction site were synthesized, and the chromosomal DNA of *E. coli* W strain (ATCC9637) was used as a template to amplify ORF (approximately 900 bp) of the cscK gene by PCR. At this time, PCR was performed with same manner of Example 1.

```
SEQ ID NO. 5:
5'-atgccatatgtcagccaaagtatg-3'

SEQ ID NO. 6:
5'-atgcactagtattacctgcctgtcg-3'
```

Primers (below SEQ ID NOs. 7 and 8) capable of amplifying the *Corynebacterium ammoniagenes*-derived pcj7 promoter and having a 5'-terminal SpeI restriction site and a 3'-terminal NdeI restriction site were synthesized, and the chromosomal DNA of *Corynebacterium ammoniagenes* strain was used as a template to amplify the promoter region of approximately 300 bp by PCR. At this time, PCR was performed under the conditions including denaturation at 94° C. for 5 min, 30 cycles of denaturation at 94° C. for 30 seconds, annealing at 56° C. for seconds, polymerization at 72° C. for 30 seconds, and then polymerization at 72° C. for 7 minutes.

SEQ ID NO. 7:
5'-atgcactagtatagggagcgttgac-3'

SEQ ID NO. 8:
5'-atgccatatgtgtttcctttcg-3'

In addition, primers (below SEQ ID NOs. 9 and 10) capable of amplifying the *Corynebacterium glutamicum*-derived lysCP1 promoter and having a 5'-terminal SpeI restriction site and a 3'-terminal NdeI restriction site were synthesized, and the chromosomal DNA of *Corynebacterium glutamicum* strain was used as a template to amplify the promoter region of approximately 300 bp by PCR. At this time, PCR was performed with the same manner above of Example 3.

SEQ ID NO. 9:
5'-ttcatatgtgtgcacctttcgatcta-3'

SEQ ID NO. 10:
5'-ttactagtgattgttaatgccgatgcta-3'

The amplified polynucleotides of the fructokinase genes and the polynucleotides of the promoter regions were treated with SpeI and NdeI restriction enzymes to obtain each DNA fragment. DNA fragments of promoters and cscK gene were ligated into the DNA fragment obtained by treatment of pDZTn with the restriction enzyme SpeI using a DNA ligase so as to construct a pDZTn-pcj7_cscK vector and a pDZTn-lysCP1_cscK vector.

EXAMPLE 4

Comparison of Lysine Productivity by cscK Gene Expression-Improved Strain

An L-lysine-producing strain, *Corynebacterium glutamicum* KFCC10881 was transformed with each of the two expression vectors, pDZTn-pcj7_cscK and pDZTn-lysCP1_cscK prepared in Example 3 using an electric pulse method. The strains having replacement of fructokinase gene promoter at the transposon region on the chromosome were selected, and cultured in the same manner as in Example 2. Average concentration of the L-lysine collected therefrom was determined (Table 2).

TABLE 2

Comparison of L-lysine concentration according to introduction of promoter (unit: g/L)

| Experimental group | Strain | Average concentration of L-lysine |
|---|---|---|
| 5 | KFCC10881 | 33.2 |
| 6 | KFCC10881::pcj_7cscK | 42.1 |
| 7 | KFCC10881::lysCP1_cscK | 38.7 |

In Table 2, Experimental group 5 represents the average concentration of L-lysine collected from the strain transformed without fructokinase gene, Experimental group 6 represents the average concentration of L-lysine collected from the strain transformed with the promoter pcj7-linked fructokinase gene cscK, and Experimental group 7 represents the average concentration of L-lysine collected from the strain transformed with the promoter lysCP1-linked fructokinase gene cscK.

As shown in Table 2, the strains transformed with the fructokinase genes (Experimental groups 6 and 7) showed higher average concentration of L-lysine than the strain transformed without fructokinase gene (Experimental group 5). Among the promoters linked to the fructokinase genes, the pcj7 promoter (Experimental group 6) showed higher average concentration of L-lysine than the lysCP1 promoter (Experimental group 7).

Therefore, in order to more efficiently produce L-lysine, the use of pcj7 promoter linked to the *E. coli*-derived fructokinase gene is more preferable.

EXAMPLE 5

Analysis of Fructose Assimilation in cscK Gene Expression-Improved Strain

In the present Example, the strain was cultured in the same manner as in Example 2, and time-dependent absorbance at 562 nm and residual amounts of sucrose and fructose in the media were measured, in order to examine whether the L-lysine-producing strain transformed with the fructokinase gene shows higher fructokinase activity and higher fructose-assimilating ability (FIG. 1).

FIG. 1 is a graph showing the quantification results of sucrose and fructose present in media, after cultivation of *Corynebacterium glutamicum* transformed with fructokinase gene, in which A represents the result of culturing the strain transformed without fructokinase gene, B represents the result of culturing the strain transformed with the pcj7 promoter-linked fructokinase gene CFK, C represents the result of culturing the strain transformed with the pcj7 promoter-linked fructokinase gene cscK, and D represents the result of culturing the strain transformed with the lysCP1 promoter-linked fructokinase gene cscK, and (•) represents OD562 values measured, (■) represents the total amount of residual sucrose in the media, and (▲) represents the total amount of residual fructose in the media in A-D.

As shown in FIG. 1, the accumulation amounts of fructose in the media were increased for a predetermined time, and then reduced during the entire period of cultivation of the strains transformed with KFCC10881 (A) and KFCC10881::pcj7_CFK (B), even though there was a relative difference between the strains. On the contrary, no fructose was detected in the media during the entire period of cultivation of the strains transformed with KFCC10881::pcj7_cscK (C) and KFCC10881::lysCP1_cscK (D).

Therefore, fructose produced by hydrolysis of the sucrose present in the media can be completely phosphorylated by fructokinase expressed from the fructokinase gene of the present invention, and thus further utilized in glycolysis, thereby preventing unnecessary energy consumption in the fructose metabolism of *Corynebacterium glutamicum*.

EXAMPLE 6

Analysis of Fructokinase Activity in cscK Gene Expression-Improved Strain

In the present Example, the known method (Microbiology (2002) 148:843-852) was used to examine whether overexpression of fructokinase gene in the cell is induced by the *Corynebacterium*-derived promoter having a strong expression-inducing activity on the chromosome and enzymatic activity of fructokinase exist in the L-lysine-producing strain. The strain was cultured in LB medium for a day, and then cell pellet was obtained by centrifugation. The cell pellet was suspended in a buffer solution, and disrupted by sonication, and then the supernatant was obtained by centrifugation at high speed. The obtained supernatant was reacted with a reaction solution containing fructose, phosphoglucose isomerase, glucose-6-phosphate dehydrogenase, ATP, and NADP+, and the production amount of NADPH was determined by measuring absorbance at 340 nm to directly calculate the conversion of fructose into fructose 6-phosphate (Table 3).

TABLE 3

Changes in fructokinase activity according to introduction of promoter or gene

| Experimental group | Strain | Activity$^a$ |
|---|---|---|
| 8 | KFCC10881 | 11.90 |
| 9 | KFCC10881::pcj7_cscK | 50.55 |
| 10 | KFCC10881::lysCP1_cscK | 42.06 |
| 11 | KFCC10881::pcj7_CFK | 23.32 | a): nmol (produced fructose-6-phosphate)/min/mg (protein)

As shown in Table 3, the strains transformed with the fructokinase genes (Experimental groups 9-11) showed 1.95 to 4.24 times increased fructokinase activity than the strain transformed without fructokinase gene (Experimental group 8). Among the fructokinase genes, the cscK gene (Experimental groups 9 and 10) showed 1.80 to 2.16 times increased fructokinase activity in comparison to the known fructokinase gene (Experimental group 11).

Therefore, it can be seen that the *E. coli*-derived fructokinase gene is preferable to the known fructokinase gene.

As shown in the results of Examples 4 to 6, the strain transformed with the promoter pcj7-linked fructokinase gene cscK showed the most excellent activity in all aspects. Thus, the transformant (KFCC-10881-Pcj7_cscK) transformed with pDZTn-pcj7_cscK was designated as *Corynebacterium glutamicum* CA01-2012, and deposited at the Korean Culture Center of Microorganisms (hereinbelow, abbreviated to "KCCM") on Mar. 28, 2011 under the Accession number KCCM11183P.

EXAMPLE 7

Production of Threonine Using cscK Gene Expression-Improved Strain

The KFCC10881 strain and KFCC10881::pcj7_cscK strains deposited in Example 6 were introduced with the plasmid vector pECCG117-homthrBCE containing threonine biosynthesis- and export-related genes to prepare each transformant. Their threonine productivities were compared to each other. The plasmid vector pECCG117-homthrBCE was constructed as follows: based on the base sequences of the threonine biosynthesis gene, hom-thrB (NCgl1136, 1137, SEQ ID NO. 19), thrC (NCgl2139, SEQ ID NO. 20) and the threonine export gene, thrE (NCgl2533, SEQ ID NO. 21) of *Corynebacterium glutamicum* ATCC13032, obtained from Japanese KEGG site (//www.genome.jp/kegg/), primers were prepared for PCR amplification of each operon or gene. The template for PCR amplification was a chromosomal DNA extracted from the strain having a resistance to 3 g/l of the threonine analogue AHV (2-amino-3-hydroxy-valerate) by mutation of the parental strain, *Corynebacterium glutamicum* ATCC13032 using NTG (N-methyl-N'-nitro-N-nitrosoguanidine).

For amplification of hom-thrB operon, primers (below SEQ ID NOs. 11 and 12) having a 5'-terminal XhoI restriction site were used. After PCR, a DNA fragment of 3 kb was finally obtained. At this time, PCR was performed under the conditions including denaturation at 94° C. for 5 min, 30 cycles of denaturation at 94° C. for 30 seconds, annealing at 56° C. for 30 seconds, polymerization at 72° C. for 3 minutes, and then polymerization at 72° C. for 7 minutes. The DNA fragment was cleaved with XhoI, and then ligated into the plasmid vector pECCG117 that was dephosphorylated after restriction with the identical enzyme, so as to construct a pECCG117-homthrB vector.

SEQ ID NO. 11:
5'-ttcctcgaggagggaacttgatcagagga-3'

SEQ ID NO. 12:
5'-ttcctcgagctacacagctgcccatttgtg-3'

For amplification of thrC gene, primers (below SEQ ID NOs. 13 and 14) having a 5'-terminal SalI restriction site were used. After PCR, a DNA fragment of 2.1 kb was finally obtained. At this time, PCR was performed under the conditions including denaturation at 94° C. for 5 min, 30 cycles of denaturation at 94° C. for 30 seconds, annealing at 56° C. for 30 seconds, polymerization at 72° C. for 2 minutes, and then polymerization at 72° C. for 7 minutes. The DNA fragment was cleaved with SalI, and then ligated into the plasmid vector pECCG117-homthrB that was dephosphorylated after restriction with the identical enzyme, so as to construct a pECCG117-homthrBC vector.

SEQ ID NO. 13:
5'-ttcgtcgacgattaaggatttcaactgcgg-3'

SEQ ID NO. 14:
5'-ttcgtcgacgcaacgagcaattccgagagc-3'

For amplification of thrE gene, primers (SEQ ID NOs. 15 and 16) having a 5'-terminal BamHI restriction site were used. After PCR, a DNA fragment of 2.5 kb was finally obtained. At this time, PCR was performed with same manner of Example 1. The DNA fragment was cleaved with BamHI, and then ligated into the plasmid vector pECCG117-homthrBC that was dephosphorylated after restriction with the identical enzyme, so as to construct a pECCG117-homthrBCE vector.

SEQ ID NO. 15:
5'-atcggatccaagatctagtcatcaatc-3'

SEQ ID NO. 16:
5'-cggcaaggatcctcctgagtg-3'

An L-lysine-producing strain, *Corynebacterium glutamicum* KFCC10881 or KFCC10881::pcj7_cscK strain was transformed with the pECCG117-homthrBCE using an electric pulse method. The strain was cultured in the same manner as in Example 2. Production amount of L-threonine according to the presence and absence of cscK gene was analyzed (Table 4).

TABLE 4

Comparison of L-threonine average concentration according to introduction of fructokinase gene (unit: g/L)

| Experimental group | Strain | Average concentration of L-threonine |
|---|---|---|
| 12 | KFCC10881/pECCG117-homthrBCE | 12.2 |

TABLE 4-continued

Comparison of L-threonine average concentration according to introduction of fructokinase gene (unit: g/L)

| Experimental group | Strain | Average concentration of L-threonine |
|---|---|---|
| 13 | KFCC10881::pcj7_cscK/ pECCG117-homthrBCE | 14.0 |

As shown in Table 4, the strains transformed with the fructokinase genes (Experimental group 13) showed higher concentration of L-threonine than the strain transformed without fructokinase gene (Experimental group 12).

Therefore, it can be seen that the strain transformed with the *E. coli*-derived fructokinase gene can be also preferably used in the production of L-threonine.

EXAMPLE 8

Comparison of Glutamate Productivity by cscK Gene Expression-Improved Strain A transformed strain was prepared by insertion of cscK gene in the chromosome of the glutamate-producing strain, and its glutamate productivity was compared. The glutamate-producing strain, *Corynebacterium glutamicum* KTCC10774 (Korean Patent No. 0824457) was transformed with the pDZTn-pcj7_cscK vector using an electric pulse method to prepare a transformant. The strains having insertion of fructokinase gene at the transposon region on the chromosome were selected.

To 250 ml of a corner-baffle flask containing 25 ml of seed medium (pH 7.0, Example 2), a loop of the strain was inoculated and cultured by shaking at 220 rpm and 30° C. for 20 hours.

Next, to 250 ml of a corner-baffle flask containing 25 ml of production medium, 1 ml of seed culture liquid was seeded and cultured by shaking at 220 rpm and 30° C. for 40 hours. At this time, the production medium (pH 7.1) had the following composition: sucrose 30 g, molasses or pretreated molasses (as reducing sugar) 10 g, $MgSO_4$ $7H_2O$ 0.4 g, $KH_2PO_4$ 1 g, $(NH_4)_2SO_4$ 3 g, $FeSO_4$ $7H_2O$ 10 mg, $MnSO_4$ $5H_2O$ 10 mg, biotin 500 ug, thiamine HCl 2 mg, urea 1 g (based on 1 L of processing water). Finally, the cultivation was terminated, and production amount of L-glutamate was determined by HPLC (Table 5).

TABLE 5

Comparison of L-glutamate average concentration according to introduction of fructokinase gene (unit: g/L)

| Experimental group | Strain | Average concentration of L-glutamate |
|---|---|---|
| 14 | KFCC10774 | 11.2 |
| 15 | KFCC10774::pcj7_cscK | 15.8 |

As shown in Table 5, the strains transformed with the fructokinase genes (Experimental group 15) showed higher concentration of L-glutamate than the strain transformed without fructokinase gene (Experimental group 14).

Therefore, it can be seen that the strain transformed with the *E. coli*-derived fructokinase gene can be also preferably used in the production of L-glutamate.

The invention claimed is:

1. *Corynebacterium* sp. for producing L-amino acids, comprising a fructokinase gene from *Escherichia* sp. operably linked to a gene expression unit, wherein the fructokinase gene has a nucleotide sequence of SEQ ID NO: 17 or SEQ ID NO: 18.

2. The *Corynebacterium* sp. for producing L-amino acids according to claim 1, wherein the gene expression unit is operably linked to a vector, and included in *Corynebacterium* microorganism by transformation or included by insertion into the chromosome of *Corynebacterium* microorganism.

3. The *Corynebacterium* sp. for producing L-amino acids according to claim 1, wherein the gene is overexpressed by modification of gene expression regulatory region.

4. The *Corynebacterium* sp. for producing L-amino acids according to claim 3, wherein the regulatory region is promoter which is selected from the group consisting of a cscK promoter, a mak promoter, a pcj7 promoter, a lysCP1 promoter, an EF-Tu promoter, a groEL promoter and an aceAB promoter.

5. The *Corynebacterium* sp. for producing L-amino acids according to claim 1, wherein the L-amino acid is L-lysine, L-threonine, or L-glutamate.

6. The *Corynebacterium* sp. for producing L-amino acids according to claim 1, wherein the *Corynebacterium* sp. is further transformed with a vector including threonine biosynthesis- and export-related genes.

7. The *Corynebacterium* sp. for producing L-amino acids according to claim 6, wherein the threonine biosynthesis-related gene is hom-thrB or hom-thrC, and the threonine export-related gene is hom-thrE.

8. The *Corynebacterium* sp. for producing L-amino acids according to claim 1, wherein the *Corynebacterium* sp. is selected from the group consisting of *Corynebacterium glutamicum*, *Corynebacterium thermoaminogenes*, *Brevibacterium flavum*, and *Brevibacterium fermentum*.

9. A method for producing an L-amino acid, comprising the steps of:
   (i) culturing the *Corynebacterium* sp. of claim 1; and
   (ii) collecting the L-amino acid from the culture.

10. The method according to 9, wherein the L-amino acid is L-lysine, L-threonine, or L-glutamate.

11. A method for producing an L-amino acid, comprising the steps of:
   (i) culturing the *Corynebacterium* sp. of claim 1 in a medium containing sucrose as a carbon source; and
   (ii) collecting the L-amino acid from the culture.

* * * * *

UNITED STATES PATENT AND TRADEMARK OFFICE
CERTIFICATE OF CORRECTION

PATENT NO. : 9,267,161 B2
APPLICATION NO. : 14/007941
DATED : February 23, 2016
INVENTOR(S) : Hyun Won Bae et al.

Page 1 of 1

It is certified that error appears in the above-identified patent and that said Letters Patent is hereby corrected as shown below:

In the Claims
Column 29, Lines 17-21
"1. *Corynebacterium* sp. for producing L-amino acids, comprising a fructokinase gene from *Escherichia* sp. operably linked to a gene expression unit, wherein the fructokinase gene has a nucleotide sequence of SEQ ID NO: 17 or SEQ ID NO: 18." should read, --1. A *Corynebacterium* sp. for producing L-amino acids, comprising a fructokinase gene from *Escherichia* sp. operably linked to a gene expression unit, wherein the fructokinase gene has the nucleotide sequence of SEQ ID NO: 17 or SEQ ID NO: 18.--.

Signed and Sealed this
Twenty-first Day of June, 2016

Michelle K. Lee
*Director of the United States Patent and Trademark Office*